(12) United States Patent
Hawkins

(10) Patent No.: US 7,705,616 B2
(45) Date of Patent: Apr. 27, 2010

(54) SENSOR FOR SENSING MOISTURE IN SOILS

(75) Inventor: Alfred J. Hawkins, Riverside, CA (US)

(73) Assignee: Irrometer Company, Inc., Riverside, CA (US)

( * ) Notice: Subject to any disclaimer, the term of this patent is extended or adjusted under 35 U.S.C. 154(b) by 254 days.

(21) Appl. No.: 12/316,026

(22) Filed: Oct. 5, 2007

(65) Prior Publication Data
US 2009/0206853 A1 Aug. 20, 2009

(51) Int. Cl.
G01R 27/08 (2006.01)

(52) U.S. Cl. .......................... 324/696; 73/73
(58) Field of Classification Search ................ 324/696
See application file for complete search history.

(56) References Cited

U.S. PATENT DOCUMENTS

| 5,179,347 | A | * | 1/1993 | Hawkins | 324/696 |
| 5,430,384 | A | * | 7/1995 | Hocker | 324/694 |
| 5,601,236 | A | * | 2/1997 | Wold | 239/63 |
| 6,468,931 | B1 | * | 10/2002 | Reeder et al. | 442/381 |
| 6,601,440 | B1 | * | 8/2003 | Chuang | 73/73 |
| 2005/0081441 | A1 | * | 4/2005 | Mantovani | 47/67 |

* cited by examiner

Primary Examiner—Timothy J Dole
Assistant Examiner—Benjamin M Baldridge
(74) Attorney, Agent, or Firm—Ladas & Parry LLP

(57) ABSTRACT

The invention relates to, in a sensor comprising: an electrically conductive metal housing, said housing having an inside wall forming a transmission matrix cavity, said wall having perforations therethrough; a liner transmissible of water lining said inside wall and covering said perforations; a transmission matrix filling said liner; a tablet of slowly dissolving material atop said transmission matrix; a cap closing said housing forming an electrode matrix chamber; an electrode chamber matrix in said electrode matrix chamber; a pair of spaced-apart electrodes in said electrode matrix chamber in contact with said electrode chamber matrix; the cap passing electrical leads from said electrodes; an improvement comprising said liner comprising a layer of laid, thermally bonded fibers in a pattern such as to provide-passages of such size as to confine said transmission matrix but to permit flow of moisture to and from said transmission matrix and soil in contact with it.

10 Claims, 2 Drawing Sheets

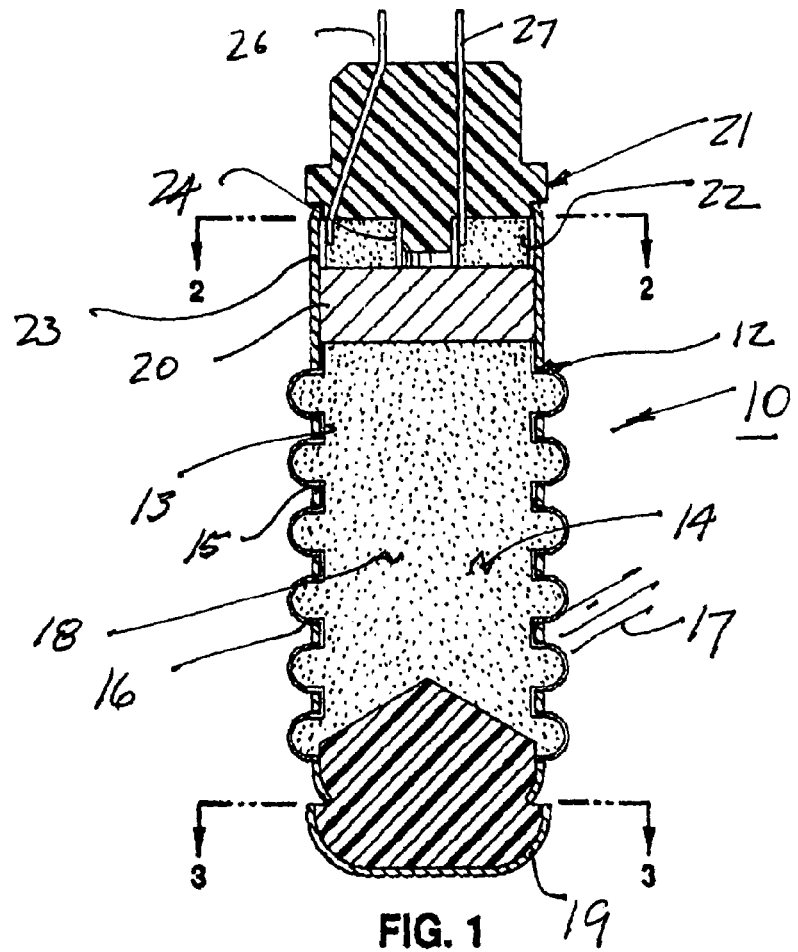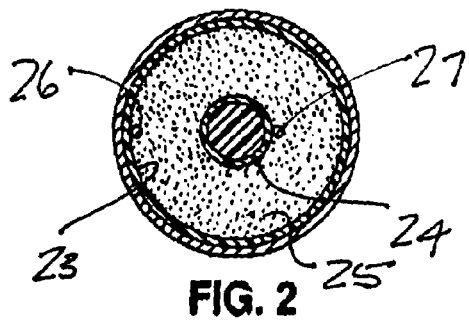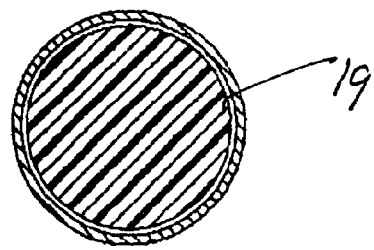
FIG. 1
FIG. 2
FIG. 3

SENSOR FOR SENSING MOISTURE IN SOILS

FIELD OF THE INVENTION

A sensor responsive to presence and amounts of moisture content in soils, with more immediate response to changes in the moisture content of the soil as they occur.

BACKGROUND OF THE INVENTION

U.S. Pat. No. 5,179,347 which issued Jan. 12, 1993 to Alfred J. Hawkins shows a classical electrical sensor for sensing moisture in soils. This patent is incorporated herein in its entirety for its showing of a soil moisture sensor of which this invention is an improvement. Details of construction for most of the sensor of this invention can be learned from this patent. The related product has been manufactured and sold for many years by Irrometer Company, Inc., at Riverside Calif. This invention is an improvement on this already-proved product, providing an improved response to changes in soil moisture as the moisture flows both inwardly and outwardly of the sensor when the soil becomes wetter or drier as irrigation, weather conditions, and plant transportation change.

Within its effective range the sensor provides useful information regarding the wetness of the soil at the depth where the sensor is placed. Depending on the crop, the depths at which the sensor is buried may be relatively shallow for row crops, or very deep near the roots of established trees, or in between these depths for other crops.

The sensor includes a strong perforated housing to resist external physical loads and to confine its contents. It is preferably made of an electrically conductive metal to provide some screening against stray electrical currents in the soil. An internal cavity contains a porous transmission matrix, usually tightly packed silica sand. A liner to be described fits inside the housing and forms an interface between the soil and the transmission matrix while it also confines the matrix to the cavity and passes moisture from the soil into the matrix, and from the matrix into the soil.

A slightly soluble buffer tablet is placed atop the transmission matrix, and beneath an electrode chamber matrix. A pair of electrodes is placed in the electronic chamber, spaced apart from one another by electrode chamber matrix. Circuit leads extend from these electrodes for connection to measurement instruments.

The concentration of water in soil (wetness) is learned by measuring the electrical resistance of the path between the electrodes. In addition to information about actual wetness current information whether the soil is becoming wetter or drier and how rapidly is important to the grower. The more responsive the sensor is to the soil condition, both temporally and accurately, the better.

It is an object of this invention to provide an improvement to the interface between the soil and the transmission matrix. One of the functions of the interface is to retain the transmission matrix inside the housing, an obviously necessary function. This function is provided in the Hawkins patent by a liner inside the housing. The other function of the interface is optimally to transfer moisture to-or from the transmission matrix from or to the soil so the wetness of the transmission matrix will approximate or equal the wetness of the soil.

In the Hawkins patent the interface is a liner made of a woven medium. It is a filter in the sense that it retains particles of a given size and larger. This material has sufficient strength for structural purposes, and open passages through which the moisture can flow. Depending on the liner material, the liner may itself become involved in the transmission of moisture by itself soaking and drying out. This delays the transmission of moisture during the time that some of the moisture soaks the matrix and stays in it, or leaves the filter material drier. This can cause a delay in response while the interface material itself adjusts to the change in wetness just at the time of most interest.

It is an object of this invention to provide for this sensor a liner made of fibers having limited capacity for moisture, randomly laid and bonded, not woven, in a pattern with passages of various and irregular cross-sections all of which will retain the silica sand but as a group is less likely to become clogged by these particles, than an orderly weave of porous filter paper As a consequence the moisture is more readily transferred through the liner into and out of the transmission matrix. When provided, a hydrophilic surface appears to facilitate passage of the moisture through the liner. Substantial absorption or loss of moisture in the interface material itself is avoided by limiting the depth of hydrophilic layer when this layer has the property of limited absorption of the water and laying it atop a cord of material that does not absorb water.

BRIEF DESCRIPTION OF THE INVENTION

A soil moisture sensor according to this invention includes a perforated rigid housing resistant to crushing by external loads. Preferably it is made of an electrically conductive metal or metal alloy.

The housing forms an internal cavity that is filled with a transmission matrix, usually silica sand. A liner fits inside the cavity, bearing against its inside wall, closing the perforations and retaining the transmission matrix. It provides an interface between the matrix and the soil.

A buffer tablet is atop the transmission matrix, An electrode chamber overlays the transmission matrix chamber and tablet. It contains a pair of spaced-apart electrodes both of which are in contact with an electrode chamber matrix, which in turn is atop and receives moisture from the transmission matrix through the tablet.

Moisture from soil bearing against the sensor and against the liner through the perforations is transferred by the liner to the transmission matrix, which in turn transfers the moisture to the buffer tablet and through it to the electrode chamber matrix and the electrodes.

According to a feature of to this invention the liner is fibrous, and substantially non-absorptive of water, the fiber being laid, not woven, and bonded to form a structurally reliable interface with passages of various and irregular cross-sections.

According to a preferred but optional future of the invention, the fibers are provided with a hydrophilic surface, this surface being formed on a skin surrounding a substantially non-absorptive core, the skin being relatively thin so as to limit the amount of moisture that can be absorbed by the fiber.

The above and other features of this invention will be fully understood from the following detailed description and the accompanying drawings, in which:

BRIEF DESCRIPTION OF THE DRAWINGS

FIG. 1 is an axial cross-section of a sensor according to this invention;

FIG. 2 is a cross-section taken at line 2-2 in FIG. 1;

FIG. 3 is a cross-section taken at line 3-3 in FIG. 1;

DETAILED DESCRIPTION OF THE INVENTION

Figure 4:
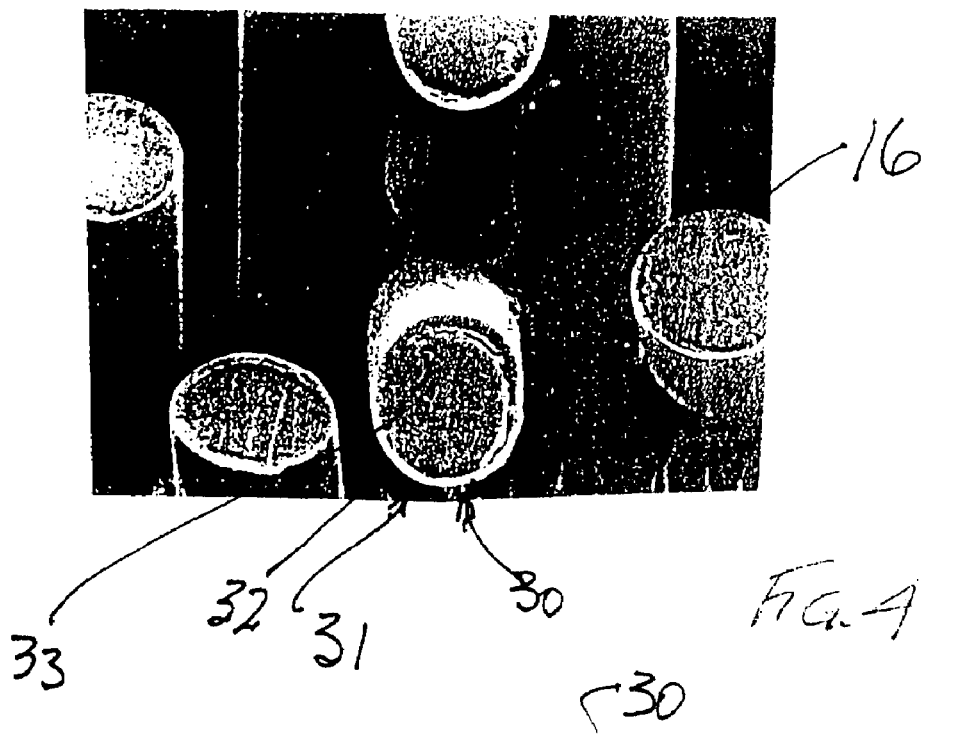
FIG. 4 is a cross-section taken at a random place in FIG. 1 showing the fiber construction.

Sensor 10 shown in the FIGS. 1-3 is an improvement over the sensor shown in Hawkins U.S. Pat. No. 5,179,347, which patent is incorporated herein in its entirety for its showing of a sensor of this type and its of its general function. The patent may be referred to for details of construction except for the liner. This invention comprises an improvement to the liner in the said Hawkins patent.

Sensor 10 includes a strong electrically conductive metal housing 12 with an inside wall 13. This wall has perforations 15 through it, that forms an internal cavity 14 usually circular, A liner 16 bears against the inside surface of wall 13 and forms an interface between soil 17 in which this sensor is buried and a transmission matrix 18 which fills the cavity. The transmission matrix bears against the liner. A closure 19 closes the bottom end of the sensor.

The transmission matrix is granular and insoluble, usually silica sand tightly packed into the liner. The transmission matrix is provided in a suitable granular size. It distends the liner into the perforations so the soil can make a firm contact with the liner. Moisture in the soil is thereby passed through the liner into the transmission matrix for measurement purposes.

The existence of at least some ions is necessary for the instrument to function as a conductance device. Some water may have insufficient conductivity for the sensor to function. To assure presence of ions, a buffer tablet 20 of a slowly-soluble material is provided for the water that is received from the transmission matrix.

In this invention and in the said Hawkins patent, the tablet is gypsum (calcium sulphate). It is placed atop and in intimate contact with the transmission matrix, so that moisture from the matrix will be provided to the tablet. In turn, minor but sufficient amounts of the gypsum will be dissolved as the moisture passes through it so as to provide a conductive ionic solution (in addition to whatever ions were in the water initially). Thus, even if the water from the soil were equivalent to distilled water, a very unlikely event, there would still be an ionic content in the water that passed through the tablet to be read by the sensor because of ions contributed by the tablet.

A cap 21 is fixed to the top of the housing to close it. It forms an electrode chamber 22 opening out the transmission matrix chamber through the tablet. It houses a pair of electrodes 23,24, which are coaxial metal cylinders, electrode 24 being inside of electrode 23.

The electrodes are packed in an electrode chamber matrix 25 which is preferably in contact with and overlaying the tablet. Electrode chamber matrix is also in contact with the electrodes. Electrical leads 26,27 are connected to respective electrodes 23,24, and pass through cap 21 to any desired instrumentation. The electrode chamber matrix is conveniently, although not necessarily made of the same material as the transmission matrix.

Figure 5:
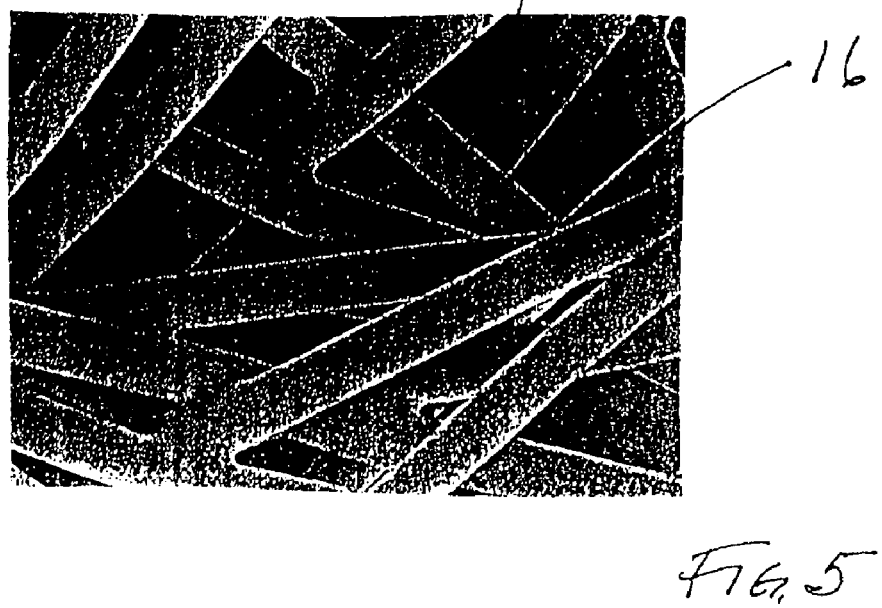
FIG. 5 is a microscopic photograph of a random section of the liner.

FIGS. 4 and 5 are enlarged microscopic photographs of a portion of liner 16 to illustrate its construction. This liner is made of thermally bonded laid fibers. It is not woven. The process of laying these fibers and thermally bonding them results in a sheet having openings in a desired size ratio so as to act as a screen. This is an art practiced by manufacturers of these products. They provide a suitably uniform open structure with resistance to deformation, substantially identical in all directions in the sheet. The fibers terminate in ends which extend to restrain particles.

In the preferred embodiment, each fiber 30 has an outer surface 31 on a skin 32 of a substance for purposes to be described below, and a solid core 33 of a different substance for a different purpose to be described.

In some embodiments the skin may be a layer of the same material as the core or continuous with the core.

The use of a hydrophilic material for skin 32 appears to facilitate the passage of water through the openings in the liner, by exerting less resistance to the flow.

In addition, the use of a material less likely to absorb and retain water lessens or eliminates lag time in the response of the sensor, because the liner itself draws water into itself when dry and becoming wet, or slowing the drying of the matrix while releasing water to the soil.

Nylon does absorb some water, but it offers the advantages of a hydrophilic surface and a surface that can be bonded. Using a polyester core with a relatively thin polyamide cladding for a skin inside it provides both advantages, but in a thin layer.

As shown in FIG. 4 the core 33 provides the major cross-section and gives the fiber its tensile strength. The skin may be of a different substance and be quite thin, it being supplied for surface properties but with very shallow depth. In this arrangement the material of the core may be much stronger than the material of the skin, but whether it is a skin of the same material as the core, or merely a continuance of the core material, it must be amenable to thermal bonding with itself so as to form an integral sheet.

In FIG. 4, the core is a polyester and the skin is a polyamide (nylon). The primary property of the core is for strength, with no particular regard to the surface properties or to the tendency of the material to water. Also, its surface is unlikely to be hydrophilic.

The skin material is a polyamide, preferably nylon. This material is generally hydrophilic, which is a substantial advantage, although not essential to this invention. It is absorptive of water, which is a reason to make the skin thin. For purposes of this invention, a suitable product for the liner can be obtained from Colback, Inc. Sand Hill Road, Enka, N.C. 28728 under its mark COLBACK® particularly its product WHD100.

The diameter of the fiber is about 40 um. The diameter of the core 33 is about 30 um. The radial thickness of the skin is about 5 um This invention is not to be limited by the embodiment shown in the drawings and described in the description, which is given by way of example and not of limitation, but only in accordance with the scope of the appended claims.

I claim:

1. In a sensor comprising:
an electrically conductive metal housing, said housing having an inside wall forming a transmission matrix cavity, said wall having perforations therethrough;
a liner, transmissible of water, lining said inside wall and covering said perforations;
a transmission matrix filling said liner;
a tablet of slowly dissolving material atop said transmission matrix;
a cap closing said housing forming an electrode matrix chamber;
an electrode chamber matrix in said electrode matrix chamber; and
a pair of spaced-apart electrodes in said electrode matrix chamber in contact with said electrode chamber matrix; the cap passing electrical leads from said electrodes; the improvement comprising:

said liner comprising a layer of laid, thermally bonded fibers in a pattern such as to provide-passages of such size as to confine said transmission matrix but to permit flow of moisture to and from said transmission matrix and soil in contact with it.

2. Apparatus according to claim 1 in which said fibers have a hydrophilic surface.

3. Apparatus according to claim 1 in which said fibers have a surface which can be self-bonded to a like surface.

4. Apparatus according to claim 3 in which said fibers have a hydrophilic surface.

5. Apparatus according to claim 4 in which said surface comprises a polyamide.

6. Apparatus according to claim 5 in which said surface is nylon.

7. Apparatus according to claim 1 in which said fibers comprise a core of polyester and a skin of polyamide substance.

8. Apparatus according to claim 7 in which the radius of the core is at least three times the thickness of the skin.

9. Apparatus according to claim 1 in which said laid, thermally bonded fibers are randomly laid and bonded in a pattern with passages of various and irregular cross-sections.

10. Apparatus according to claim 9, wherein said pattern with passages of various and irregular cross-sections are such that said laid, thermally bonded fibers retain the transmission matrix filling but as a group are less likely to become clogged by the transmission matrix filling than a regularly patterned liner.

* * * * *